(12) United States Patent
Wakahara

(10) Patent No.: US 10,314,552 B2
(45) Date of Patent: Jun. 11, 2019

(54) BED APPARATUS AND X-RAY COMPUTED TOMOGRAPHY APPARATUS

(71) Applicant: Toshiba Medical Systems Corporation, Otawara-shi (JP)

(72) Inventor: Masayuki Wakahara, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 254 days.

(21) Appl. No.: 15/280,373

(22) Filed: Sep. 29, 2016

(65) Prior Publication Data

US 2017/0095219 A1  Apr. 6, 2017

(30) Foreign Application Priority Data

Oct. 2, 2015 (JP) ................................ 2015-196388
Sep. 26, 2016 (JP) ................................ 2016-186947

(51) Int. Cl.
*A61B 6/04* (2006.01)
*A61B 6/03* (2006.01)

(52) U.S. Cl.
CPC ............ *A61B 6/0407* (2013.01); *A61B 6/032* (2013.01); *A61B 6/0457* (2013.01)

(58) Field of Classification Search
CPC ..... A61B 6/0407; A61B 6/032; A61B 6/0457; A61B 6/461; A61B 6/5205
USPC .................................................... 378/20, 208
See application file for complete search history.

(56) References Cited

U.S. PATENT DOCUMENTS

2006/0104422 A1* 5/2006 Iisaku ...................... A61B 6/04
                                                                378/209

FOREIGN PATENT DOCUMENTS

| JP | 3-24110 U | 3/1991 |
|---|---|---|
| JP | 4-138140 | 5/1992 |
| JP | 4-166136 | 6/1992 |
| JP | 6-38958 | 2/1994 |
| JP | 8-140963 | 6/1996 |
| JP | 2007-111150 | 5/2007 |

\* cited by examiner

*Primary Examiner* — Courtney D Thomas
(74) *Attorney, Agent, or Firm* — Oblon, McClelland, Maier & Neustadt, L.L.P.

(57) ABSTRACT

A bed apparatus according to one embodiment, includes a top plate, a first slide actuator, an elevating actuator, and a second slide actuator. The first slide actuator supports the top plate to be slidable in the longitudinal direction. The elevating actuator supports the first slide actuator to be movable in the vertical direction, and is installed on the floor. The second slide actuator is provided between the first slide actuator and the elevating actuator and supports the first slide actuator such that the first slide actuator is slidable interlockingly with the vertical movement of the elevating actuator.

12 Claims, 6 Drawing Sheets

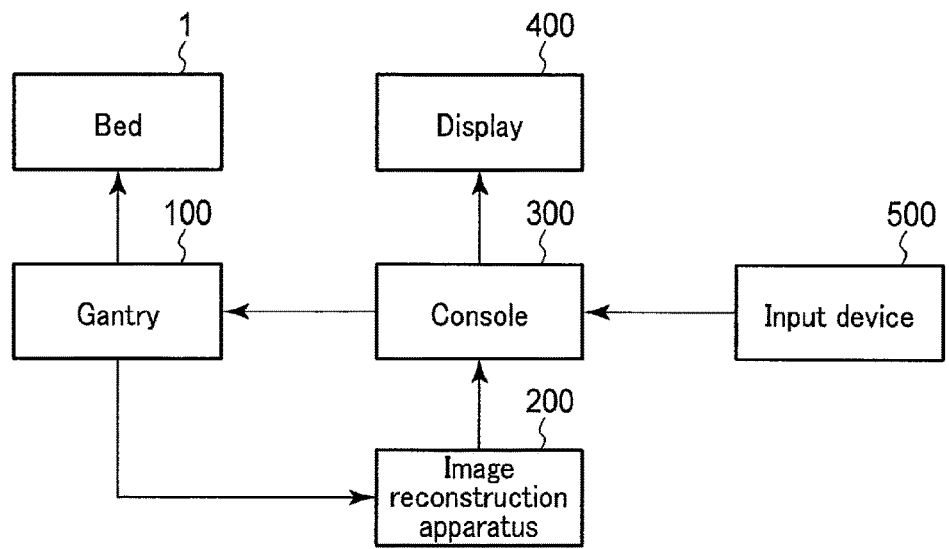
F I G. 1
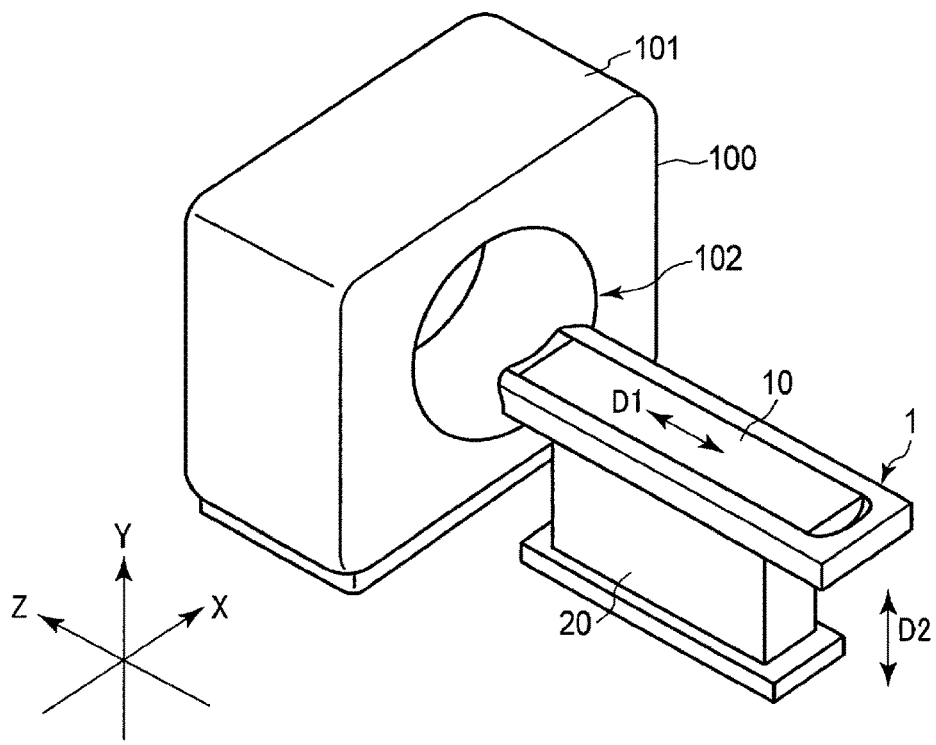
F I G. 2

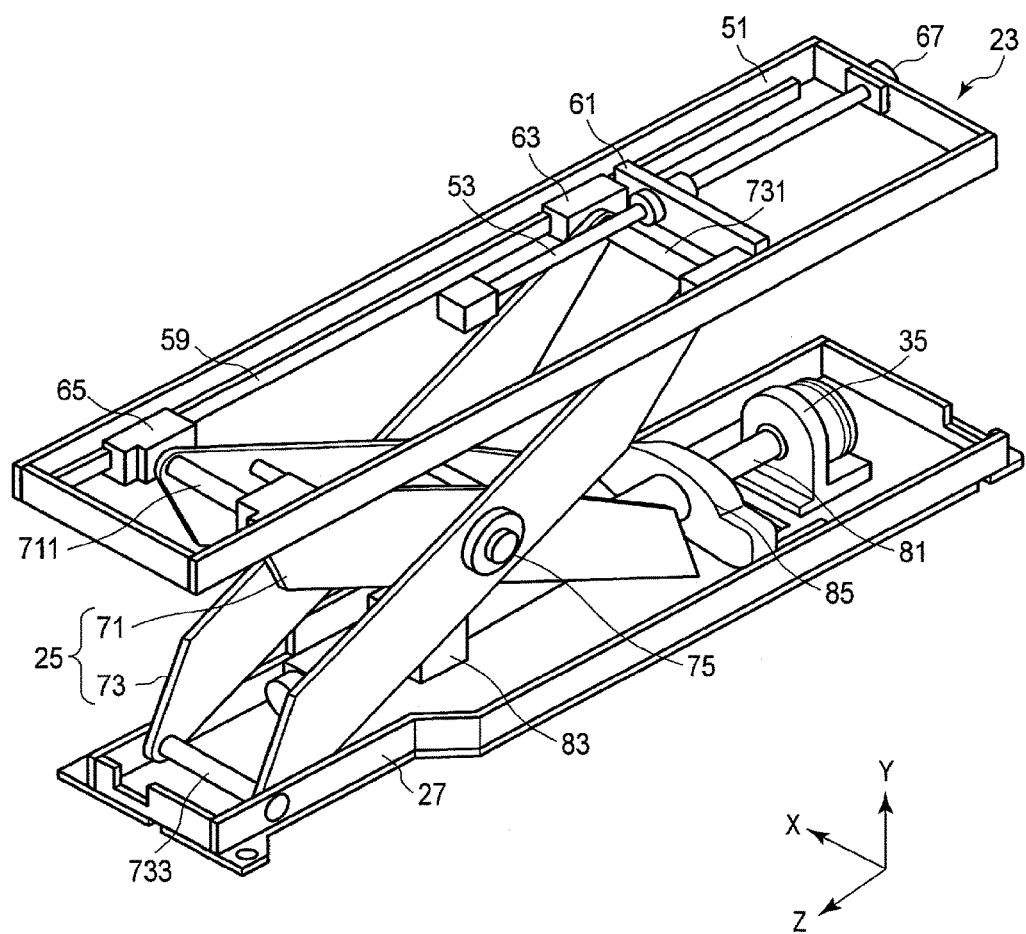
F I G. 4

BED APPARATUS AND X-RAY COMPUTED TOMOGRAPHY APPARATUS

CROSS-REFERENCE TO RELATED APPLICATIONS

This application is based upon and claims the benefit of priority from prior Japanese Patent Application No. 2015-196388, filed Oct. 2, 2015, and prior Japanese Patent Application No. 2016-186947, filed Sep. 26, 2016, the entire contents of all of which are incorporated herein by reference.

FIELD

Embodiments described herein relate generally to a bed apparatus and an X-ray computed tomography apparatus.

BACKGROUND

An X-ray computed tomography apparatus is provided with a gantry and a bed. In the state where a top plate is slid in the bore of the gantry, a CT scan is performed such that a to-be-imaged portion of a subject lying on the top plate can be included in the imaging range.

The bed supports the top plate at one end in the slice direction. With this structure, the front portion of the top plate tends to sag in accordance with an increase in the amount by which the top plate is slid into the bore of the gantry. If the top plate sags as above, the subject may be shown at a displaced position in a reconstructed image, resulting in a wrong diagnosis being made.

BRIEF DESCRIPTION OF THE DRAWINGS

FIG. 1 schematically shows a configuration of an X-ray computed tomography apparatus according to the present embodiment.

FIG. 2 schematically shows the outward appearance of the gantry and bed employed in the present embodiment.

FIG. 4 is a perspective view of a lower slide actuator, an elevating actuator and a base employed in the present embodiment.

DETAILED DESCRIPTION

Figure 3:
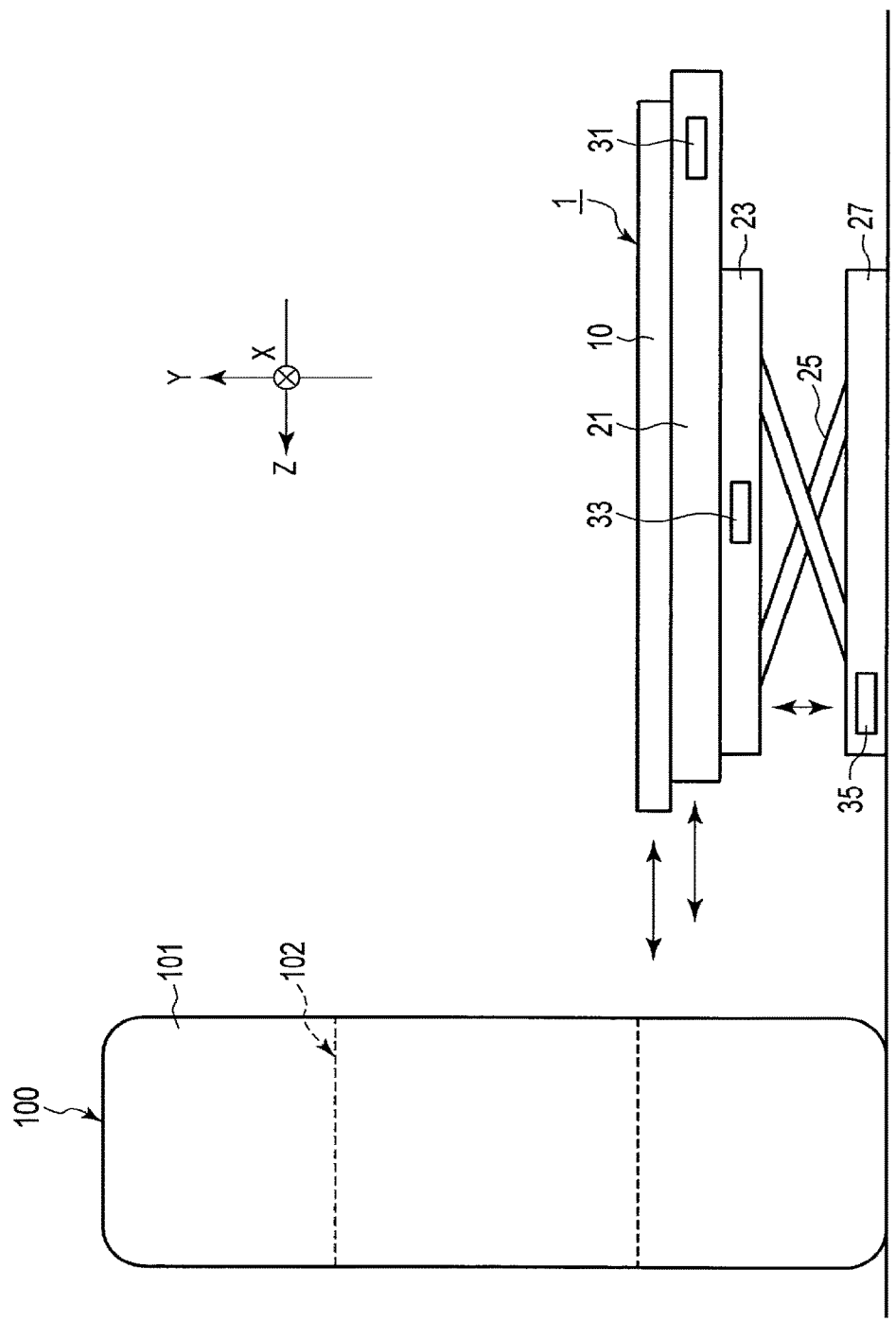
FIG. 3 schematically shows side faces of the gantry and bed employed in the present embodiment.

The bed apparatus of the present embodiment comprises a top plate, a first slide actuator, an elevating actuator, and a second slide actuator. The first slide actuator supports the top plate to be slidable in the longitudinal direction. The elevating actuator supports the first slide actuator to be movable in the vertical direction, and is installed on the floor. The second slide actuator is provided between the first slide actuator and the elevating actuator and supports the first slide actuator such that the first slide actuator is slidable interlockingly with the vertical movement of the elevating actuator.

The bed apparatus and the X-ray computed tomography apparatus of the present embodiment will be described with reference to the accompanying drawings.

FIG. 1 schematically shows a configuration of the X-ray computed tomography apparatus of the present embodiment. As shown in FIG. 1, the X-ray computed tomography apparatus of the present embodiment includes a gantry 100, a bed 1, an image reconstruction apparatus 200, a console 300, a display 400 and an input device 500. The gantry 100 and the bed 1 are installed in an examination room, for example. The image reconstruction apparatus 200, the console 300, the display 400 and the input device 500 are installed in a control room adjacent to the examination room. FIG. 2 schematically shows the outward appearance of the gantry 100 and bed 1 of the present embodiment.

As shown in FIGS. 1 and 2, the gantry 100 has a housing 101 having a substantially cylindrical bore 102, which functions as an imaging space. The housing 101 contains a rotating frame (not shown) for which an X-ray tube (not shown) and an X-ray detector (not shown) are provided, with the bore 102 located in between. The rotating frame is supported by a main frame to be rotatable around the central axis of the bore 102. When the gantry 100 is driven, X-rays are emitted from the X-ray tube, with the rotating frame rotating around the central axis. The X-rays emitted from the X-ray tube and passing through the subject are detected by the X-ray detector, and are converted into raw data representing the intensity of the detected X-rays. The raw data is transmitted to the image reconstruction apparatus 200 by means of, for example, a non-contact data transmission apparatus provided for the gantry 100.

The bed 1 is installed in front of the gantry 100. The bed 1 is provided with a top plate 10 and a top plate support 20. The top plate support 20 supports the top plate 10 such that the top plate 10 is slidable in the longitudinal direction D1 thereof and movable in the vertical direction D2. The top plate support 20 has a cantilevered structure. To be specific, the top plate support 20 supports the top plate 10 only on one side with respect to the longitudinal direction D1. The top plate 10 is arranged such that the central axis thereof is parallel to the central axis of the bore 102. The bed 1 operates under the control of the gantry 100. It is assumed here that an axis parallel to the longitudinal direction D1 of the top plate 10 is defined as Z axis, and an axis parallel to the vertical direction is defined as Y axis. An axis perpendicular to both the Z axis and the Y axis is defined as Z axis. The XYZ coordinate system is a Cartesian coordinate system.

The image reconstruction apparatus 200 is a computer apparatus provided with a processor and a memory. Based on the raw data transmitted from the gantry 100, the image reconstruction apparatus 200 reconstructs a CT image representing a spatial distribution of the X-ray attenuation by the subject. The data on the CT image is supplied to the console 300. The console 300 is a computer apparatus provided with a processor and a memory. The console 300 serves as the nerve center of the X-ray computed tomography apparatus. The console 300 controls the gantry 100 to perform a CT scan. The console 300 also performs image processing for the data on the CT image. The display 400 and the input device 500 are connected to the console 300. As the display 400, a CRT display, a liquid crystal display, an organic EL display, a plasma display, etc. can be used. The console 300 displays a CT image and various setting windows on the display 400. The input device 500 is a known input device, including a keyboard, a mouse and various switches. The console 300 performs processing in accordance with an operation of the input device 500. The image reconstruction apparatus 200 may be incorporated in the console 300.

The term "processor" used in the above descriptions is, for example, a central processing unit (CPU) or a graphics processing unit (GPU), or may include the following types of circuitry: application-specific integrated circuitry (ASIC), a programmable logic device (such as a simple programmable logic device (SPLD), a complex programmable logic device (CPLD), or a field programmable gate array (FPGA)), or the like. The processor reads the programs stored in the memory and executes them to realize the respective functions.

FIG. 3 schematically shows side faces of the gantry 100 and bed 1 employed in the present embodiment. In FIG. 3, the housing of the bed 1 is not depicted. As shown in FIG. 3, the bed 1 is provided in front of the gantry 100. In FIG. 3, the initial state of the bed 1 is shown. The initial state refers to the state where the top plate 10 is at the lowest level. The lowest level is the lower limit of the movable range in which the top plate 10 is movable in the Y direction. In the initial state, the bed 1 is arranged at a position such that a space allowing a user (e.g., a medical person) to pass is provided between the bed 1 and the gantry 100.

As shown in FIG. 3, the bed 1 includes a top plate 10, an upper slide actuator 21, a lower slide actuator 23, an elevating actuator 25 and a base 27. A subject lies on the top plate 10. The top plate 10 is a soft, plate-like structure. Desirably, the top plate 10 is formed of a material having a comparatively high X-ray transmission rate, such as urethane foam or carbon.

The top plate 10 is supported by the upper slide actuator 21 to be slidable in the Z direction. The upper slide actuator 21 may have any structure as long as it enables the top plate 10 to slide. For example, the upper slide actuator 21 includes a rigid support frame (not shown) for supporting the top plate 10, and a guide rail (not shown) provided on the support frame and configured to guide the top plate 10 in the Z direction. The upper slide actuator 21 is connected to a motor (hereinafter referred to as an upper motor) 31 which generates a force causing the top plate 10 to slide along the guide rail. The upper motor 31 is realized, for example, by an existing type of motor such as a servo motor. The upper motor 31 operates under the control of bed control circuitry 41 mentioned below.

The upper slide actuator 21 is supported by a lower slide actuator 23 to be slidable in the Z direction. The lower slide actuator 23 may have any structure as long as it enables the upper slide actuator 21 to slide. For example, the lower slide actuator 23 may be realized by a ball screw. The detailed structure of the lower slide actuator 23 will be described later. The lower slide actuator 23 is connected to a motor (hereinafter referred to as a lower motor) 33 which generates a force causing the upper slide actuator 21 to slide in the Z direction. The lower motor 33 is realized, for example, by an existing type of motor such as a servo motor. The lower motor 33 operates under the control of the bed control circuitry 41, which will be mentioned later.

The lower slide actuator 23 is supported by the elevating actuator 25 to be vertically movable in the Y direction. The elevating actuator 25 may have any structure as long as it enables the lower slide actuator 23 to move vertically. For example, the elevating actuator 25 may be realized by X links. The detailed structure of the elevating actuator 25 will be described later. The elevating actuator 25 is provided on the base 27 installed on the floor. The base 27 is realized by a rigid metal frame. The elevating actuator 25 is connected to a motor (hereinafter referred to as a vertical motor) 35 which generates a force causing the lower slide actuator 23 to move in the Y direction. The vertical motor 35 is realized, for example, by an existing type of motor such as a servo motor. The vertical motor 35 operates under the control of the bed control circuitry 41, which will be mentioned later.

Figure 5:
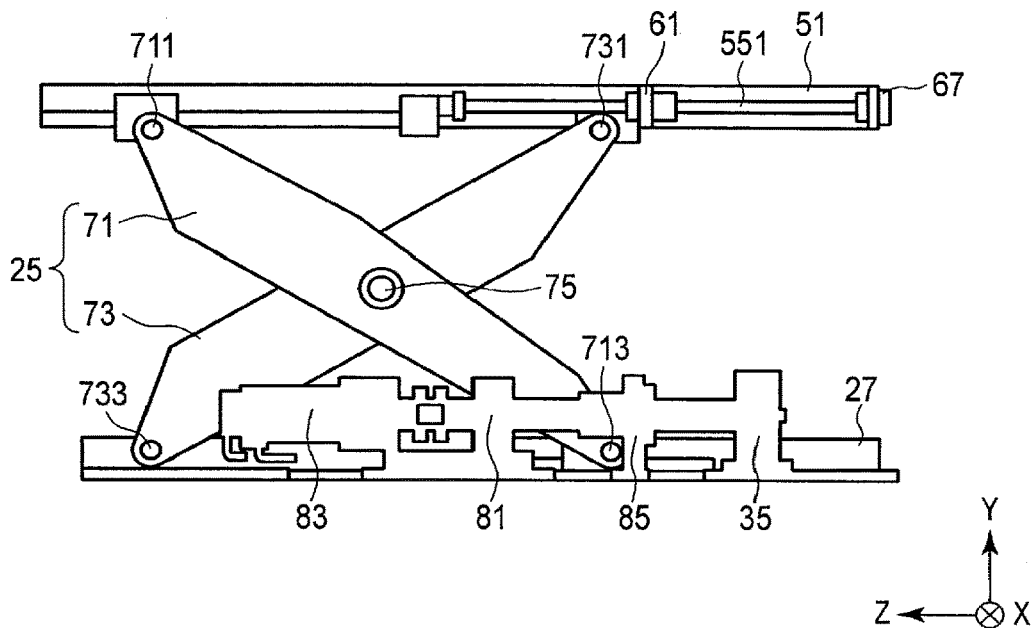
FIG. 5 is a longitudinal section showing the lower slide actuator, elevating actuator and base employed in the present embodiment.

FIG. 4 is a perspective view of the lower slide actuator 23, elevating actuator 25 and base 27. FIG. 5 is a longitudinal section of the lower slide actuator 23, elevating actuator 25 and base 27.

As shown in FIGS. 4 and 5, the lower slide actuator 23 includes a support frame 51, for example. The support frame 51 is a rectangular metal frame elongated in the Z direction. The support frame 51 includes a ball screw 53. The ball screw 53 includes a screw shaft and a slider. The ball screw 53 is attached to the support frame 51 and extends in the Z direction. The upper slide actuator 21 is attached to the slider of the ball screw 53. The support frame 51 is provided with a guide rail 59 for guiding the sliding movement of the ball screw 53 in the Z direction. One end of the ball screw 53 is coupled to the support frame 51 to be rotatable on the axis. The screw shaft of the ball screw 53 rotates on the axis interlockingly with the rotation of the rotating shaft of the lower motor 33 (not shown in FIG. 4). The slider of the ball screw 53 slides in the axial direction of the screw shaft (namely, in the Z direction) interlockingly with the rotation of the screw shaft. The ball screw 53 may be provided with a stopper 61 for mechanically restricting the movable range of the ball screw 53.

In the above, the support frame 51 was described as having a rectangular shape. However, the present embodiment is not limited to this. For example, the support frame 51 may be replaced with a pair of beam-like frames to which a guide rail 59 is attached. In this case, a pair of frames corresponding to the short-side direction (X direction) of the rectangle of the support frame 51 do not have to be provided.

The elevating actuator 25 may be realized, for example, by X links. Each X link 25 includes a pair of links which are pivotally coupled in the shape of "X" and which are made up of link 71 (hereinafter referred to as a movable link) and link 73 (hereinafter referred to as a fixed link). The movable link 71 and the fixed link 73 are rotatable relative to each other, with a fulcrum 75 as a center. The movable link 71 and the fixed link 73 are made, for example, by a pair of metal plates having substantially the same length. The distance between the support-frame-side end portion 711 of the movable link 71*b* and the fulcrum 75, the distance between the base-side end portion 713 of the movable link 71 and the fulcrum 75, the distance between support-frame-side end portion 731 of the fixed link 73 and the fulcrum 75, and the distance between the base-side end portion 733 of the fixed link 73 and the fulcrum 75 are designed to be substantially the same.

The base-side end portion 733 of the fixed link 73 is fixed to the base 27. The end portion 733 may be fixed, using a fastening tool or the like; alternatively, the end portion 733 may be fitted and secured in a concave of the base 27. The other end portion 731 of the fixed link 73 is fixed to the support frame 51. To be more specific, the end portion 731 is fixed to a roller 63, which is provided for each of a pair of frames corresponding to the long sides of the rectangle of the support frame 51. The roller 63 is fixed to the guide rail 59 by means of a fastening tool or the like. With this structure, the end portion 731 is fixed to the support frame 51. The end portion 731 may be fitted and secured in a concave of the support frame 51.

The base-side end portion 713 of the movable link 71 is slidably supported by the base 27. To be more specific, a lead screw 81 is inserted between the end portions 713. One end of the lead screw 81 is connected to the vertical motor 35. The vertical motor 35 is arranged on the base 27. A brake 83 is attached to the other end of the lead screw 81. A nut 85 is provided between the end portion 733 of the lead screw 81 and the vertical motor 35. The nut 85 is a structure member having a through hole 81, and a thread groove engageable with the thread of the lead screw 81 is formed in the through hole. The nut 85 threadably engages with the lead screw 81.

The other end portion 711 of the movable link 71 is slidably supported by the support frame 51. To be more specific, the other end portion 711 is fixed to a roller 65, which is provided for each of a pair of frames corresponding to the long sides of the rectangle of the support frame 51. The roller 65 is slidably coupled to the guide rail 59.

That is, the guide rail 59 of the support frame 51 enables the ball screw 53 (namely, the upper slide actuator 21) to slide in the Z direction and also enables the movable link 71 to slide in the Z direction. In comparison with the case where the slide movement of the ball screw 53 (upper slide actuator 21) in the Z direction and the slide movement of the movable link 71 in the Z direction are guided by respective rails, the bed 1 of the present embodiment can be reduced in the height dimension.

The lead screw 81 rotates on its axis interlockingly with the rotation the vertical motor 35 makes around the axis of rotation. The nut 85 slides in the axial direction of the lead screw 81, namely, in the Z direction, interlockingly with the rotation of the lead screw 81. For example, when the lead screw 81 rotates forward, the nut 85 slides in the +Z direction, and when the lead screw 81 rotates rearward, the nut 85 slides in the −Z direction.

When the nut 85 slides in the +Z direction, the movable link 71 is pushed in the +Z direction. Since the distance between the movable link 71 and the fixed link 73 is shortened in the Z direction, the support frame 51 ascends in the Y direction. When the nut 85 slides in the −Z direction, the movable link 71 is released from the pushing force acting in the +Z direction. Since the distance between the movable link 71 and the fixed link 73 is lengthened in the Z direction, the support frame 51 descends in the Y direction.

Figure 6:
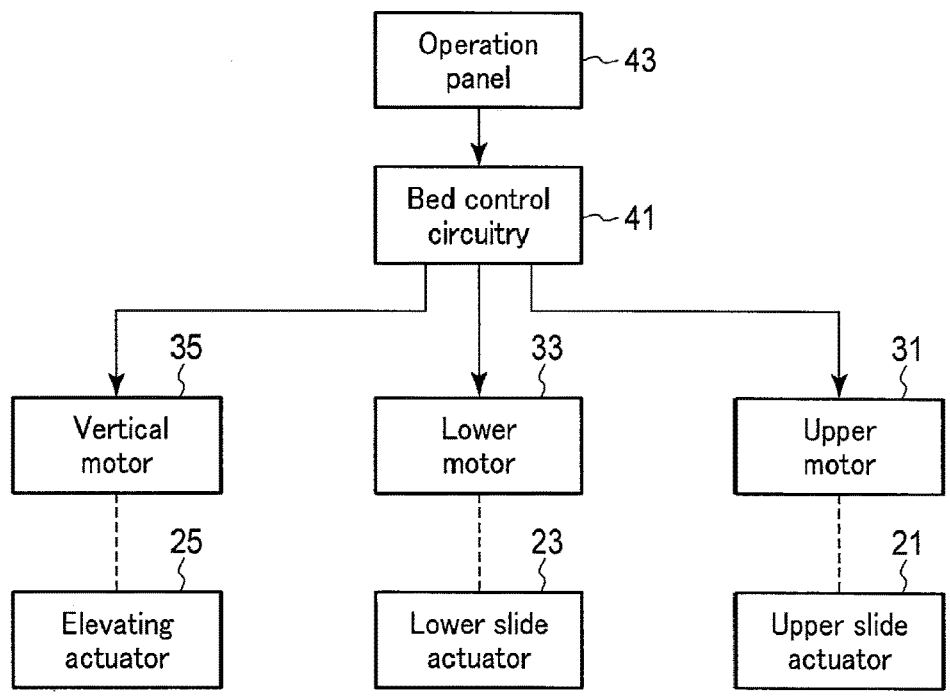
FIG. 6 shows a configuration of a bed driving system employed in the X-ray computed tomography apparatus of the present embodiment.

A description will now be given of the bed driving system of the X-ray computed tomography apparatus of the present embodiment. FIG. 6 illustrates a configuration of the bed driving system of the X-ray computed tomography apparatus of the present embodiment. As shown in FIG. 6, the X-ray computed tomography apparatus of the present embodiment comprises an upper motor 31, an upper slide actuator 21, a lower motor 33, a lower slide actuator 23, a vertical motor 35, an operation panel 43 and bed control circuitry 41.

The upper motor 31 is connected to the upper slide actuator 21. The upper motor 31 is driven in response to a driving signal supplied from the bed control circuitry 41. The lower motor 33 is connected to the lower slide actuator 23. The lower motor 33 is driven in response to a driving signal supplied from the bed control circuitry 41. The vertical motor 35 is connected to the elevating actuator 25. The vertical motor 35 is driven in response to a driving signal supplied from the bed control circuitry 41.

The operation panel 43 is provided for either the bed 1 or the gantry 100. The operation panel 43 includes various buttons used for instructing the movement of the bed 1. For example, the operation panel 43 includes an insert button for instructing the slide movement of the top plate 10 in the +Z direction, a retreat button for instructing the slide movement of the top plate 10 in the −Z direction, an ascend button for instructing the ascending movement of the top plate 10 in the +Y direction, and a descend button for instructing the descending movement of the top plate in the −Y direction.

The bed control circuitry 41 receives instruction signals corresponding to button operations on the operation panel 43 and controls the upper motor 31, the lower motor 33 and the vertical motor 35. The bed control circuitry 41 includes, as hardware resources, a processor such as a central processing unit (CPU) or a micro processing unit (MPU), and a memory such as a read only memory (ROM) or a random access memory (RAM). The bed control circuitry 41 may be realized by an application specific integrated circuit (ASIC), a field programmable gate array (FPGA), a complex programmable logic device (CPLD) or a simple programmable logic device (SPLD). The processor reads the programs stored in the memory and executes them to realize the functions mentioned above. The programs may be incorporated in the circuitry of the processor, instead of storing them in the memory. In this case, the processor reads the programs incorporated in its circuitry and executes them to realize the functions. The bed control circuitry 41 is provided for either the bed 1 or the gantry 100. Alternatively, the bed control circuitry 41 may be provided for the console 300 or for a computer dedicated to controlling the bed 1.

When the insert button is depressed, the bed control circuitry 41 drives the upper slide actuator 21 to slide the top plate 10 in the +Z direction. Instead of driving only the upper slide actuator 21, the bed control circuitry 41 may synchronously drive both the upper slide actuator 21 and the lower slide actuator 23 to slide the top plate 10 in the +Z direction. When the retreat button is depressed, the bed control circuitry 41 drives the upper slide actuator 21 to slide the top plate 10 in the −Z direction. Instead of driving only the upper slide actuator 21, the bed control circuitry 41 may synchronously drive both the upper slide actuator 21 and the lower slide actuator 23 to slide the top plate 10 in the −Z direction. When the ascend button is depressed, the bed control circuitry 41 drives the elevating actuator 25 to ascend the top plate 10 in the +Y direction. When the descend button is depressed, the bed control circuitry 41 drives the elevating actuator 25 to descend the top plate 10 in the −Y direction.

Figure 7:
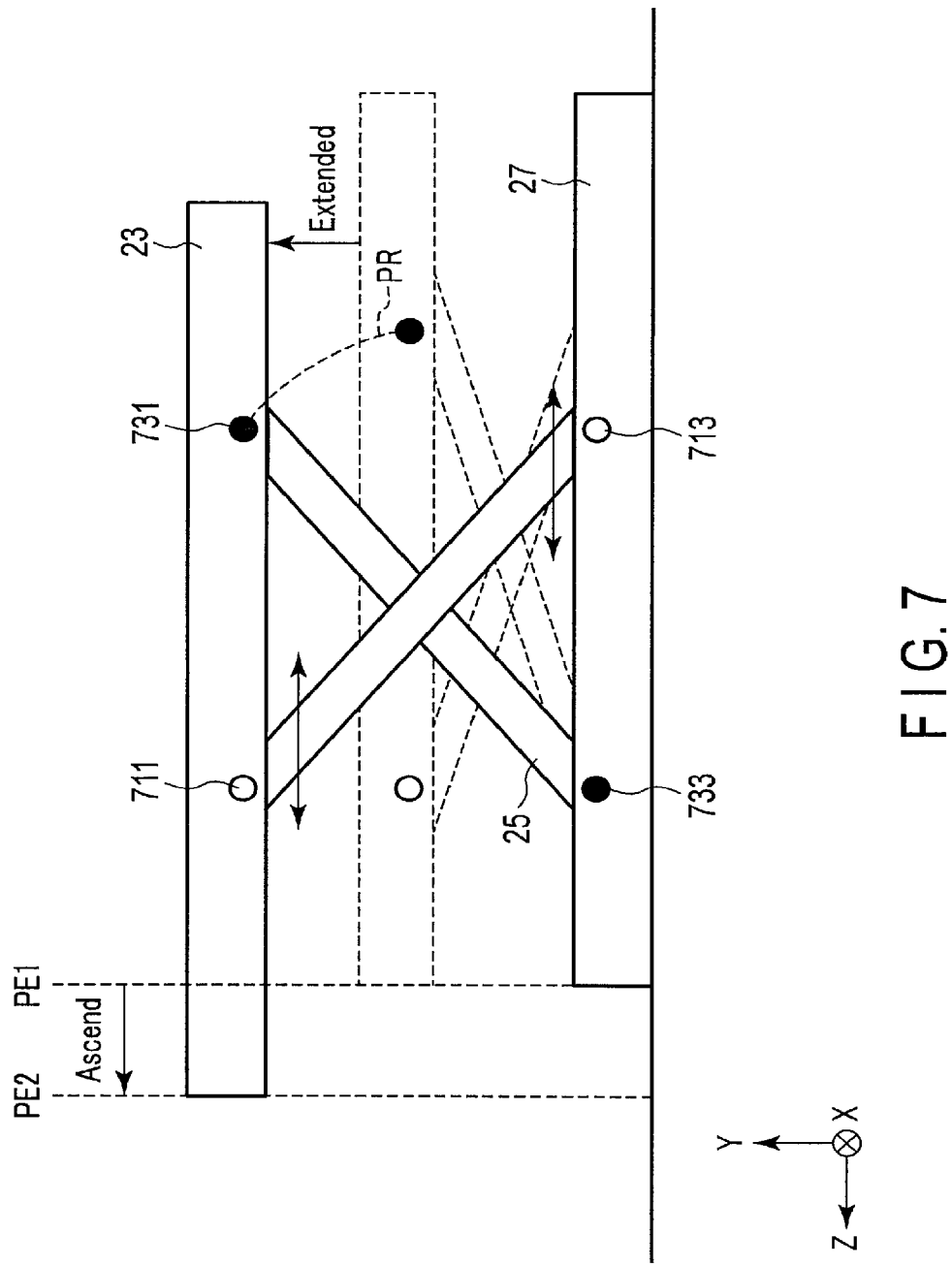
FIG. 7 illustrates the movement of the lower slide actuator and the elevating actuator according to the present embodiment.

A description will now be given of an operation example of the bed 1 employed in the present embodiment. FIG. 7 illustrates a movement of the lower slide actuator and the elevating actuator according to the present embodiment. In FIG. 7, the bed 1 in the initial state is indicated by broken lines, and the bed 1 in the ascended state is indicated by solid lines.

As shown in FIG. 7, in the initial state, a Z-direction end of the lower slide actuator 23 (precisely, a Z-direction end of the support frame 51 of the lower slide actuator 23) is at position PE1 determined in the Z direction. When an ascend instruction is issued from the operation panel 43, the bed control circuitry 41 drives the vertical motor 35 in accordance with the ascend instruction. The lead screw 81 rotates on its axis interlockingly with the forward rotation of the vertical motor 35. Interlockingly with the rotation of the lead screw 81, the nut 85 slides in the +Z direction and pushes the movable links 71. Since the movable links 71 are pushed by the nut 85, the movable links 71 and the fixed links 73 rotate around the fulcrum 75 such that the distance between the movable links 71 and the fixed links 73 is shortened in the Z direction.

As described above, end portion 711 of each movable link 71 is provided for the lower slide actuator 23 to be slidable in the Z direction, and end portion 713 thereof is provided for the base 27 to be slidable in the Z direction. End portion 731 of each fixed link 73 is fixed to the lower slide actuator 23, and end portion 733 thereof is fixed to the base 27. With this structure, when each movable link 71 is pushed by the nut 85, end portion 731 moves along arc PR (the radius of which is the linear line connecting end portion 731 and end portion 733), with end portion 733 as the fulcrum. During this movement, the positional relationship of end portion 731 with the lower slide actuator 23 and the positional relationship of end portion 733 with the base 27 remain unchanged. Accordingly, the Z-direction end of the lower slide actuator 23 extends in the +Z direction, namely toward the gantry 100, when the movable links 71 are pushed in the Z direction. For example, when the top plate has ascended to a target height, the Z-direction end of the lower slide actuator 23 is at position PE2, which is closer to the gantry 100 than position PE1 where the Z-direction end is located in the initial position.

Figure 8:
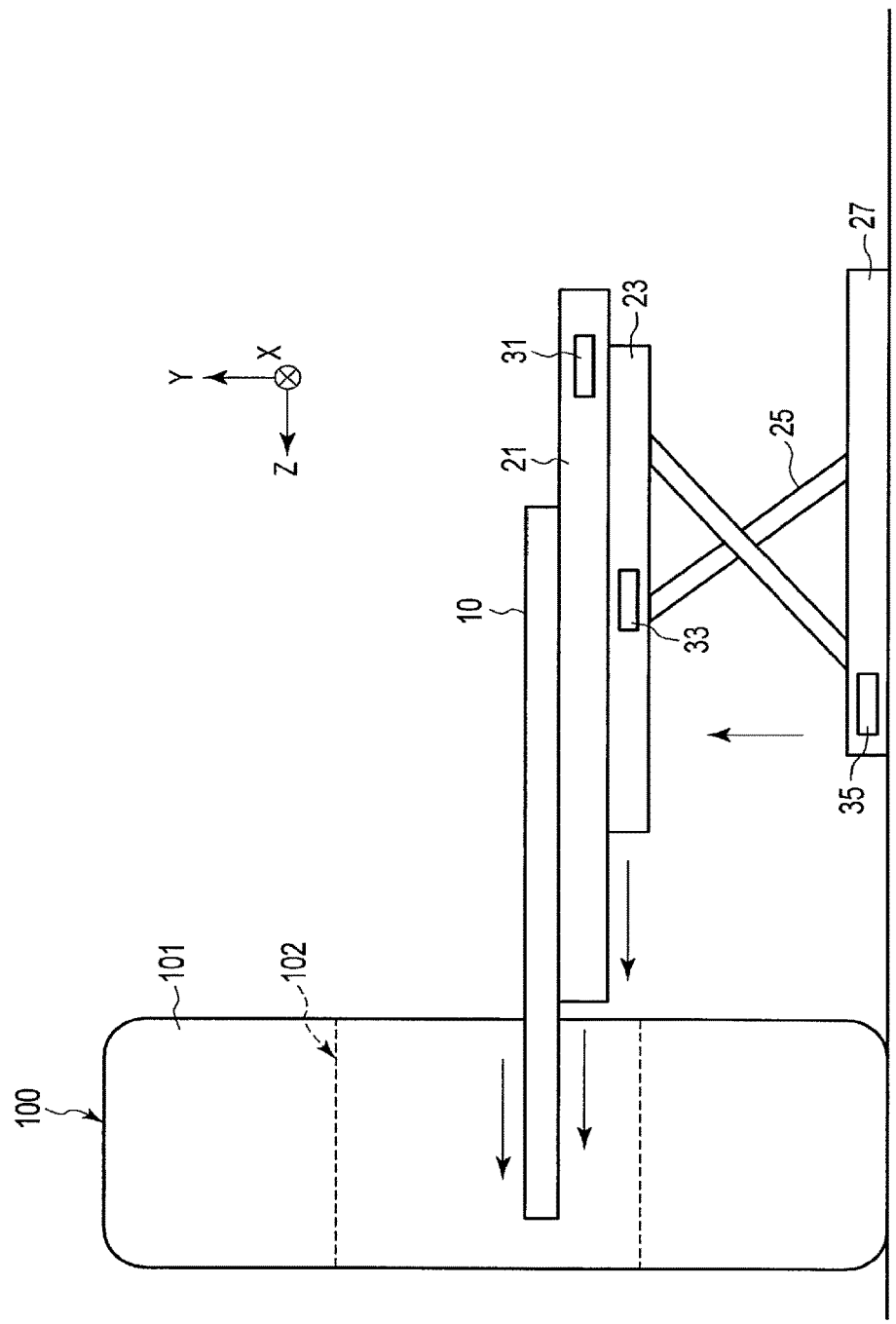
FIG. 8 illustrates the movement of the bed for positioning the top plate, according to the present embodiment.

FIG. 8 illustrates a movement of the bed 1 for positioning the top plate. When the ascend button (for ascending the top plate 10) of the operation panel 43 is depressed, the bed control circuitry 41 drives the vertical motor 35 such that the distance between the movable link 71 and the fixed link 73 of the X link 25 is shortened. In accordance with a decrease in the distance between the movable link 71 and the fixed link 73, the lower slide actuator 23 extends toward the gantry 100. The vertical motor 35 is driven until the top plate 10 reached a height position where it can be inserted into the bore 102. When the insert button (for inserting the top plate 10) of the operation panel 43 is depressed, the bed control circuitry 41 drives the lower motor 33 to slide the upper slide actuator toward the gantry 100. When the Z-direction end of the upper slide actuator 21 reaches a position near the bore of the gantry 100, the bed control circuitry 41 stops driving the lower motor 33 and drives the upper motor 31 to slide the top plate 10 toward the scan plane inside the bore 102. The upper motor 31 is driven until the target portion of the subject lying on the top plate 10 is included within the FOV. Instead of individually driving the upper motor 31 and the lower motor 33, the bed control circuitry 41 may synchronously drive both the upper motor 31 and the lower motor 33.

In the above, the ascend button and the insert button were described as being depressed for insertion into the bore 102. However, the present embodiment is not limited to this. For example, the operation panel 43 may include an auto insert button, which enables the top plate 10 in the initial state to be inserted into the bore 102 in response to a one-touch operation. When the auto insert button is depressed, the bed control circuitry 41 synchronously drives the upper motor 31 and the lower motor 33 such that the top plate 10 ascends in the Y direction and is inserted into the bore 102.

As shown in FIGS. 4 and 5, a brake 67 for braking the rotation of the ball screw 53 by the lower motor 33 is provided at one end of the ball screw 53. The brake 67 is switchable between a state in which the ball screw 53 is fixed and a state in which the ball screw 53 is released. For example, the brake 67 may be any type of brake, including a friction brake and an electric brake. For example, in the case of a friction brake, the brake 67 includes a braking element for suppressing the rotation of the ball screw 67 and an operation actuator for supporting the braking element and moving the braking element with reference to the ball screw 53. For example, when a fixing instruction is issued under the control of the bed control circuitry 41, the braking element 53 is pressed against the ball screw 53, and the ball screw 53 is fixed (locked) thereby. When a releasing instruction is issued under the control of the bed control circuitry 41, the braking element is moved away from the ball screw 53, and the ball screw 53 is released from the locked state.

The brake 67 may be manually switched by the user between the fixed state of the ball screw 53 and the released state thereof. For example, the brake 67 may be provided with a mechanical button coupled to the braking element. When this button is depressed, the braking element 53 is pressed against the ball screw 53, and the ball screw 53 is fixed (locked) thereby. When the button is pulled, the braking element is moved away from the ball screw 53, and the screw shaft 55 is released from the locked state.

Let us assume a case where the bed 1 is not provided with the brake 67. In this case, if the bed control circuitry 41 fails to function properly in the state where the top plate 10 is inserted in the bore 102, the top plate 10 may not be retreated in the −Z direction. If the brake 67 can be manually switched between the fixed state and the released state, the lower slide actuator 23 can be retreated in the −Z direction even if the bed control circuitry 41 of the bed fails to function properly. Accordingly, the safety of the subject is ensured.

As described above, the bed 1 of the present embodiment includes the top plate 10, the upper slide actuator 21, the elevating actuator 25 and a lower slide actuator 23. The upper slide actuator 21 supports the top plate 10 to be slidable in the Z direction. The elevating actuator 25 supports the upper slide actuator to be movable in the Y direction, and is installed on the floor. The lower slide actuator 23 is provided between the upper slide actuator 21 and the elevating actuator 25 and supports the upper slide actuator such that the upper slide actuator is slidable interlockingly with the vertical movement of the elevating actuator 25.

With the above structure, the bed 1 enables the lower slide actuator (which supports the upper slide actuator 21) to move closer to the gantry 100 interlockingly with the ascending movement of the elevating actuator 25. With the lower slide actuator extended toward the gantry 100, the lower motor 33 is driven, so that the upper slide actuator supporting the top plate 10 can be moved closer to the gantry 100. In this state, the upper motor 31 is driven to insert the top plate 10 into the bore 102. Since the upper slide actuator 21 supporting the top plate 10 thereon can be moved close to the bore 102, the front portion of the top plate 10 is prevented from sagging (in the −Y direction) inside the bore. Since the top plate is prevented from sagging, the subject never fails to appear at the right position in a reconstructed image, and a wrong diagnosis is prevented.

As described above, the bed 1 of the present embodiment includes two slide actuators, namely the upper slide actuator 21 and the lower slide actuator 23. In comparison with a bed having a single slide actuator, the bed 1 of the present embodiment is advantageous in that the upper slide actuator 21 and the lower slide actuator 23 can be short in the Z direction, provided that the movable ranges of the beds are same. To be more specific, the upper slide actuator 21 and the lower slide actuator 23 can be shortened in the Z direction by the distance by which the lower slide actuator 23 is extended in the +Z direction (i.e., the distance between position PE1 and position PE2 shown in FIG. 7). Because of this, the bed 1 of the present embodiment is small as a whole.

While certain embodiments have been described, these embodiments have been presented by way of example only, and are not intended to limit the scope. Indeed, the novel embodiments described herein may be embodied in a variety of other forms; furthermore, various omissions, substitutions and changes in the form of the embodiments described herein may be made without departing from the spirit. The accompanying claims and their equivalents are intended to cover such forms or modifications as would fall within the scope and spirit.

The invention claimed is:

1. A bed apparatus, comprising:
   a top plate;
   a first slide actuator which supports the top plate to be slidable in a longitudinal direction;
   an elevating actuator which is installed on a floor and supports the first slide actuator to be movable in a vertical direction; and
   a second slide actuator which supports the first slide actuator such that the first slide actuator is slidable in the longitudinal direction,
   wherein the first slide actuator moves toward a gantry of an X-ray computed tomography apparatus interlockingly with an upward movement of the elevating actuator during the upward movement of the elevating actuator.

2. The bed apparatus according to claim 1, further comprising:
   an upper motor which moves the top plate;
   a lower motor which moves the first slide actuator; and
   control circuitry configured to synchronously control the upper motor and the lower motor, in response to an instruction signal for moving the top plate closer to a bore of the gantry.

3. The bed apparatus according to claim 1, wherein the second slide actuator includes
   a slider attached to the first slide actuator;
   a ball screw which supports the slider to be slidable in the longitudinal direction; and
   a support frame which guides the slider to slide in the longitudinal direction.

4. The bed apparatus according to claim 3, wherein the elevating actuator includes an X link which supports the second slide actuator to be movable in a vertical direction, a base provided on the floor and supports the X link, and a second motor which generates a force for rotating the X link,
   the X link includes a pair of links pivotally coupled to each other,
   one of the links has a first end fixed to the base and a second end fixed to the support frame, and
   a remaining one of the links has a first end slidably supported by the base and a second end slidably supported by the support frame.

5. The bed apparatus according to claim 4, wherein the second slide actuator further includes a roller which is attached to the second end of the remaining one of the links and which is guided by the support frame to be slidable in the longitudinal direction.

6. The bed apparatus according to claim 4, wherein the support frame guides a sliding movement of the slider in the longitudinal direction and a sliding movement of the second end of the remaining one of the links in the longitudinal direction.

7. The bed apparatus according to claim 3, further comprising:
   a motor connected to the ball screw, the motor generating a force with which the ball screw is rotated; and
   a brake which brakes rotation of the ball screw by the motor.

8. The bed apparatus according to claim 7, wherein the brake is switchable between a state in which the ball screw is fixed and a state in which the ball screw is released.

9. The bed apparatus according to claim 1, wherein the second actuator is provided between the first slide actuator and the elevating actuator.

10. An X-ray computed tomography apparatus, comprising:
    a bed on which a subject lies and a gantry which performs CT imaging with X-rays, the bed comprising
      a top plate;
      a first slide actuator which supports the top plate to be slidable in a longitudinal direction;
      an elevating actuator which is installed on a floor and supports the first slide actuator to be movable in a vertical direction; and
      a second slide actuator which supports the first slide actuator such that the first slide actuator is slidable in the longitudinal direction,
    wherein the first slide actuator moves toward the gantry interlockingly with an upward movement of the elevating actuator during the upward movement of the elevating actuator.

11. The X-ray computed tomography apparatus according to claim 10, wherein the second actuator slides toward the gantry interlockingly with the upward movement of the elevating actuator, and
    the first actuator moves toward the gantry together with the second slide actuator.

12. The bed apparatus according to claim 1, wherein the second actuator slides toward the gantry interlockingly with the upward movement of the elevating actuator, and
    the first actuator moves toward the gantry together with the second slide actuator.

* * * * *